United States Patent [19]

Hagemann et al.

[11] Patent Number: 4,837,369

[45] Date of Patent: Jun. 6, 1989

[54] PROCESS FOR THE PREPARATION OF 3-FLUORO-2-(FLUOROMETHYL)-PROPENE

[75] Inventors: Hermann Hagemann; Bernd Baasner, both of Leverkusen, Fed. Rep. of Germany

[73] Assignee: Bayer Aktiengesellschaft, Leverkusen, Fed. Rep. of Germany

[21] Appl. No.: 18,543

[22] Filed: Feb. 25, 1987

[30] Foreign Application Priority Data

Mar. 13, 1986 [DE] Fed. Rep. of Germany ....... 3608380

[51] Int. Cl.$^4$ ....................... C07C 17/20; C07C 21/18
[52] U.S. Cl. ..................................... 570/160; 570/135
[58] Field of Search ................................ 570/160, 135

[56] References Cited

U.S. PATENT DOCUMENTS

| | | | |
|---|---|---|---|
| 2,634,301 | 4/1953 | Ruh et al. | 570/160 |
| 2,787,646 | 4/1957 | Hasseldine | 570/160 |
| 2,842,603 | 7/1958 | Miller | 570/160 |
| 2,889,379 | 6/1959 | Ruh et al. | 570/160 |
| 2,900,422 | 8/1959 | Stahl et al. | 570/160 |
| 3,287,425 | 11/1966 | Maynard | 570/160 |
| 3,655,786 | 4/1972 | Gilbert et al. | 260/653.5 |
| 3,739,036 | 6/1973 | Valicenti et al. | 260/653.3 |
| 4,220,608 | 9/1980 | Feiring | 570/160 |
| 4,533,776 | 8/1985 | Baasner et al. | 568/946 |

FOREIGN PATENT DOCUMENTS 0120575 2/1984 European Pat. Off. .
1088925 10/1967 United Kingdom .

OTHER PUBLICATIONS

"Organic Reactions", vol. 21, p. 179.
"Diels-Alder Reactions with Fluorine-containing Olefins" by E. T. McBee, C. G. Hsu, O. R. Pierce and C. W. Roberts, 2/20/55; pp. 915-916; J.A.C.S., 77,915 (1955).
"Fluorure D'Allyle", Ann. Chem. [1] 7,37488 (1894); pp. 374-375.
Halogen-Verbindungen Fluorverbindungen Herstellung, Reaktivitat Und Umwandlung Chlorverbindungen Herstellung E. Forch. W. Hahn. R. Stroh 1962, pp. 153-154.
Chemical Abstracts vol. 48, Feb. 10, 1954, No. 3, 1-Apparatus Plant Equipment, and Unit Operations 1073-1074; 1237-1238 10-Organic Chemistry.
*Bull. Soc. Chim. France*, 123-124 (1953).

*Primary Examiner*—J. E. Evans
*Attorney, Agent, or Firm*—Sprung Horn Kramer & Woods

[57] ABSTRACT

3-Fluoro-2-(fluoromethyl)-propene is prepared in a simple manner and in good yields by reacting 3-chloro-2-(chloromethyl)-propene with a fluorinating agent. The present invention also relates to 3-fluoro-2-(chloromethyl)-propene, an intermediate product in this process.

7 Claims, No Drawings

PROCESS FOR THE PREPARATION OF 3-FLUORO-2-(FLUOROMETHYL)-PROPENE

BACKGROUND OF THE INVENTION

1. Field of the Invention

The present invention relates to a process for the preparation of 3-fluoro-2-(fluoromethyl)-propene (see formula (I))

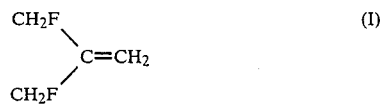

which can also be called difluoroisobutylene, and to the new compound 3-fluoro-2-(chloromethyl)-propene (see formula (II))

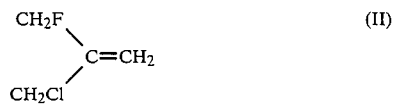

which can also be called fluoro-chloro-isobutylene.

2. Background Information

3-Fluoro-2-(fluoromethyl)-propene is a useful intermediate product for syntheses in organic chemistry, for example, in the fields of dyestuffs, pharmaceuticals, plant protection agents, plastics and textile and plastics auxiliaries. This particular olefin is particularly suitable for the synthesis of nitroaliphatics containing fluorine, which in turn can be used as precursors for the preparation of herbicides (see U.S. Pat. No. 4,533,776).

It is known that 3-fluoro-2-(fluoromethyl)-propene (I) is obtained as an undesirable by-product, as a result of pyrolytic splitting off of hydrogen chloride and formaldehyde, in a yield of only 12.7% when attempts are made to react pentaerythritol-tribromohydrin (III) with potassium fluoride to give the corresponding trifluoro compound (see *Bull. Soc. Chim. France*, 1953, 123/124). This reaction is illustrated by the following equation (1):

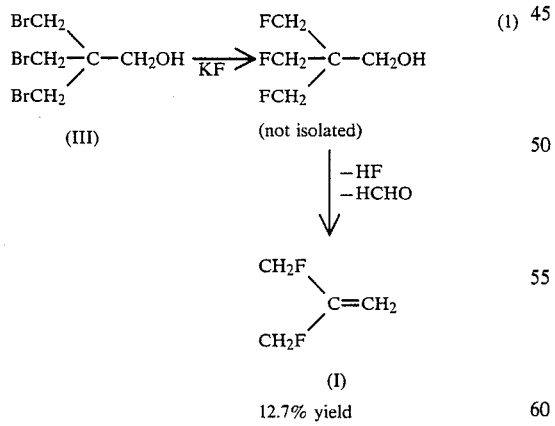

With this synthesis sequence, there is of course no possibility of preparing 3-fluoro-2-(fluoromethyl)-propene (I) on an industrial scale.

SUMMARY OF THE INVENTION

A process has now been found for the preparation of 3-fluoro-2-(fluoromethyl)-propene, which is characterized in that 3-chloro-2-(chloromethyl)-propene is reacted with a fluorinating agent. The synthesis passes through the previously unknown compound 3-fluoro-2-(chloromethyl)-propene (II) as an intermediate stage, which, with a suitable reaction procedure, for example, if a stoichiometric amount of the fluorinating agent is metered in, can also become the main product of the reaction, but otherwise is always additionally obtained as a by-product which can be separated off.

DETAILED DESCRIPTION OF THE INVENTION

The process according to the invention is illustrated by the following equation (2) by way of example:

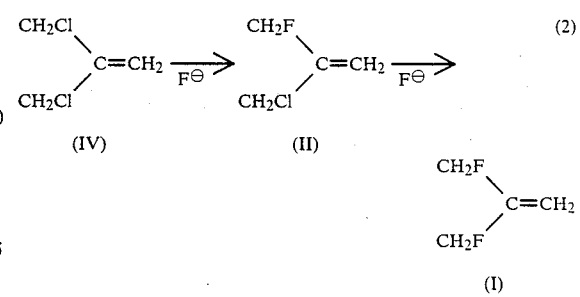

The starting compound 3-chloro-2-(chloromethyl)-propene (IV) is a known compound. It is obtained, for example, as an unavoidable product in the allyl-chlorination of isobutylene to give methallyl chloride, which is carried out on a large industrial scale. However, it can also be prepared purposefully in a good yield in accordance with Europeant Patent A No. 159,508 from methallyl chloride by reaction with sulphuryl chloride in the liquid phase.

Possible fluorinating agents for the process according to the invention are, for example, the customary fluorinating agents. In view of their good industrial and inexpensive accessibility, for example, potassium fluoride, potassium hydrogen fluoride, sodium fluoride, sodium hydrogen fluoride, calcium fluoride and magnesium fluoride, if appropriate, also as mixtures with one another and in mixtures with small amounts of cesium fluoride, are suitable. Particularly good yields are in general obtained when potassium fluoride is used. Water-containing fluorides or fluorides which have not been specially predried can also be employed in the process according to the invention. In these cases, a solvent is advantageously used and the water introduced is removed from the reaction mixture by distillation of some of the solvent, with which the water is then also removed.

Theoretically, 2 equivalents of fluorinating agent are required for the conversion of 3-chloro-2-(chloromethyl)-propene (IV) into 3-fluoro-2-(fluoromethyl)-propene (I). The fluorinating agent is preferably employed in excess, for example, in an amount of 2.01 to 2.5 equivalents, preferably in an amount of 2.03 to 2.2 equivalents, in each case based on the amount of the compound (IV) employed. Larger excesses in general lead to conversions which are only slightly higher and to only slightly reduced contents of the monofluoro compound (II) in the reaction mixture. The use of smaller amounts of fluorinating agent, for example, 0.8 to 1.5 equivalents of fluorinating agent, based on the amount of the compound (IV) employed, leads to a greater increase in the content of monofluoro compound (II) in the reaction mixture, and these amounts are used if this compound is to be purposely prepared.

The process according to the invention can be carried out at various temperatures, for example, at temperatures in the range from 80° to 300° C. Temperatures between 110° and 180° C. are preferred. The reaction according to the invention can be carried out under normal pressure or increased pressure. Increased pressure is advantageous above all if a solvent which has a boiling point under normal pressure below the intended reaction temperature is to be used. The reaction according to the invention can be carried out either continuously or discontinuously.

In general, it is advantageous to carry out the reaction according to the invention in the presence of a solvent. Suitable solvents are those which are inert or substantially inert under the reaction conditions. Possible solvents are, for example, ethers, for example ethyl propyl ether, n-butyl ethyl ether, di-n-butyl ether, diisobutyl ether, diisoamyl ether, diisopropyl ether, anisole, phenetol, cyclohexyl methyl ether, diethyl ether, tetrahydrofuran, dioxane, thioanisole and $\beta,\beta'$-dichlorodiethyl ether; polyethylene glycol ethers, such as the dimethyl ether, diethyl ether, di-n-propyl ether, diisopropyl ether, di-n-butyl ether, diisobutyl ether, di-sec.-butyl ether and di-tert.-butyl ether of ethylglycol and the dimethyl ether, diethyl ether, di-n-propyl ether, diisopropyl ether, di-sec.-butyl and di-tert.-butyl ether of diethylene glycol; analogous diethers of triethylene glycol and of tetraethylene glycol; diethylene glycol monomethyl ether, diethylene glycol monoethyl ether and triethylene glycol monobutyl ether; ethylene glycol, diethylene glycol, triethylene glycol, tetraethylene glycol, 1,2-propanediol and 1,3-propanediol; sulphoxides, such as dimethylsulphoxide, diethylsulphoxide, dimethyl sulphone, diethyl sulphone, methyl ethyl sulphone and tetramethylene sulphone (sulpholane); N-methylpyrrolidone, dimethylformamide, hexamethylphosphoric acid triamide, N,N'-dimethylpropylene urea and N-methyl-caprolactam; benzene and toluene; acetonitrile and any desired mixtures of these solvents in terms of quality and quantity. Preferred solvents are diethylene glycol, triethylene glycol, tetraethylene glycol and N-methylpyrrolidone; particularly preferred solvents are tri- and tetraethylene glycol. Any desired amounts of solvents can be employed, based on the starting compound (IV). Suitable amounts are, for example, amounts of solvents such that a 10 to 80% strength by weight mixture of the starting compound (IV) in the particular solvent or solvent mixture is present. The concentration of this mixture is preferably 35–65% by weight.

Additions of catalysts, for example crown ethers, in general have only little influence on the conversion of the starting compound (IV) and the yield of 3-fluoro-2-(fluoromethyl)-propene (I). Although the use of catalysts, for example crown ethers, is possible, it is therefore not preferred.

After the reaction according to the invention, a reaction mixture is in general present which, in addition to the difluorinated product (I), also contains monofluorinated product (II), unreacted starting substance (IV), the corresponding chloride formed from the fluorinating agent and, if appropriate, fluorinating agent employed in excess and, if appropriate, the solvent added. Working up of such reaction mixtures can be carried out in a simple manner, for example by separating the difluorinated product, the monofluorinated product, the unreacted starting substance and, if appropriate, the solvent from one another in the sequence of their boiling points by distillation. In general, the difluoro product first passes over, followed by the monofluoro product and then the unreacted substance. If a solvent is to be employed in the reaction, its boiling point is advantageously chosen so that it does not have a boiling point too close to that of one of the other components. In particular, when the preferred solvents are used, the difluorinated product, the monofluorinated product and unreacted starting substance can in many cases be distilled off out of the solvent and the latter can be separated off as the distillation residue. This separation by distillation can be carried out under normal pressure or reduced pressure. Suitable pressures are in general those from normal pressure up to about 10 mbar. Too great a reduction in pressure can have the effect that the distillates can be collected only with a relatively great cooling effort, and are therefore less advantageous. The chloride formed from the fluorinating agent and, if appropriate, fluorinating agent employed in excess can be removed by filtration before the distillation (preferred) or left in the distillation bottom product after the distillation (less preferred). Unreacted starting substance (IV), monofluorinated product (II), solvent and fluorinating agent employed in excess can be fed separately or together to a further batch for carrying out the process according to the invention. The process can also be carried out continuously, for example by continuously removing the difluorinated product (I) and the chloride formed from the fluorinating agent from the reaction mixture and topping the mixture up with corresponding amounts of starting substance (IV) and fluorinating agent. The reaction product (I) separated off in this manner or in another manner can, if appropriate, be purified by further distillation, if this is desired.

The process according to the invention enables 3-fluoro-2-(fluoromethyl)-propene (I) to be prepared in a simple manner, in good yield and in high purities. It is decidedly surprising that these results can be achieved, since according to the prior art described, starting from the saturated compound (III), only very small amounts of 3-fluoro-2-(fluoromethyl)-propene (I) can be obtained. With the use, according to the invention, of the unsaturated starting compound (IV), more side reactions were to be expected, due to the reactive double bond present, for example also oligomerization and resinification reactions, than when the saturated starting compound (III) was used.

In the context of the present invention, the new compound 3-fluoro-2-(chloromethyl)-propene of the formula (II) has furthermore been found.

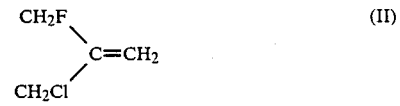

This compound can also be called fluorochloroisobutylene.

The preparation of the compound (II) and also conditions under which the compound (II) can be predominantly obtained have already been described above.

The new compound of the formula (II) can be converted, as described above, into the known compound of the formula (I), which, according to U.S. Pat. No. 4,533,776, is an intermediate product for the preparation of herbicides.

EXAMPLES

EXAMPLE 1

1.22 kg (21 mol) of potassium fluoride were taken in 1.75 l of tetraethylene glycol. To remove small amounts of entrained water, 150 ml of tetraethylene glycol were first distilled off together with this water under a pressure of 15 mbar. 1.25 kg (10 mol) of 3-chloro-2-(chloromethyl)-propene (IV) were then added and the mixture was heated under reflux for 3 hours. The volatile constituents were then distilled off from the solvent under 15 mbar into a well-cooled receiver. The resulting crude distillation was fractionated over a column under a pressure of 1,013 mbar. The following fractions were obtained:

Fraction 1: 390 g, boiling point 62°–64° C. Content of 3-fluoro-2-(fluoromethyl)-propene (I): 98.3% (according to gas chromatography).

Intermediate fraction: 50 g, boiling point 65°–98° C. Content of (I): 39.6% (according to gas chromatography), content of 3-fluoro-2-(chloromethyl)-propene (II): 57.1% (according to gas chromatography).

Fraction 2: 240 g, boiling point 98°–100° C. Content of (II): 94.3% (according to gas chromatography).

Residue: 305 g of starting material (IV) with a content of (IV) of 87.8% (according to gas chromatography).

A redistilled sample of fraction 2 (boiling point 99°–100° C., purity according to gas chromatography 99.4%) had a refractive index $n_D^{20}$ of 1.4237.

The residue, fraction 2 and the intermediate fraction was employed again in subsequent batches without further treatment.

EXAMPLE 2

2.44 kg of potassium fluoride were taken in 3.5 l of tetraethylene glycol and, to remove small amounts of entrained water, 300 ml of tetraethylene were distilled off together with this water under a pressure of 15 mbar. 2.5 kg of 3-chloro-2-(chloromethyl)-propene (IV) were then metered in at a bath temperature of 135° C. and an internal temperature of 120±3° C. in the course of 40 minutes. At the same time, the constituents which were volatile under these conditions were distilled off over a 30 cm packed column under 1,013 mbar. The mixture was then allowed to continue to react for a further 4 hours and the remainder of the volatile constituents were distilled over under a pressure of 20 mbar. The crude distillate thus obtained was fractionated over a column under a pressure of 1,013 mbar. 1.01 kg of the compound (I) were obtained with a boiling point of 61°–64° C. in a purity of 97.4% (according to gas chromatography).

EXAMPLES 3–11

The procedure followed was as in Example 1, but the reaction time, the solvents, the concentration ratios in the reaction mixture and the molar ratios of fluorinating agent to starting material were varied. All the experiments were carried out at the reflux temperature. In each case 1 mol (125 g) of 3-chloro-2-(chloromethyl)-propene (IV) was employed. The composition of the resulting crude distillate was investigated by gas chromatography. The results can be seen from the following table.

TABLE

| Example No. | Potassium fluoride [g] | Solvents ml | Reaction time [hours] | Crude distillate [g] | Composition of the crude distillate [% by weight] | | |
|---|---|---|---|---|---|---|---|
| | | | | | Compound (I) | (II) | (IV) |
| 3 | 122 | Diethylene glycol 160 | 3 | 67 | 59.9 | 31.8 | 7.1 |
| 4 | 122 | Triethylene glycol 160 | 3 | 71 | 61.7 | 30.7 | 6.2 |
| 5 | 122 | N—Methylpyrrolidone 160 | 3 | 104 | 26.1 | 47.0 | 24.9 |
| 6 | 122 | Tetraethylene glycol 160 | 5 | 61 | 82.8 | 14.3 | 1.9 |
| 7 | 122 | Tetraethylene glycol 160 | 1 | 86 | 45.4 | 40.0 | 12.0 |
| 8 | 122 | Tetraethylene glycol 250 | 3 | 68 | 87.4 | 9.8 | 1.9 |
| 9 | 174 | Tetraethylene glycol 160 | 3 | 63 | 78.3 | 14.6 | 4.1 |
| 10 | 122 | Tetraethylene glycol 110 | 3 | 64 | 66.8 | 23.9 | 6.8 |
| 11 | 122 plus 1.5 g [18]crown-6 | Tetraethylene glycol 160 | 3 | 73 | 90.8 | 6.3 | 1.8 |

It will be appreciated that the instant specification and examples are set forth by way of illustration and not limitation, and that various modifications and changes may be made without departing from the spirit and scope of the present invention.

What is claimed is:

1. A process for the preparation of 3-fluoro-2-(fluoromethyl)-propene comprising reacting 3-chloro-2-(chloromethyl)-propene with a fluorinating agent selected from the group consisting of potassium fluoride, sodium fluoride, sodium hydrogen fluoride, calcium fluoride, magnesium fluoride and mixtures thereof, wherein the process is conducted in the presence of a solvent selected from the group consisting of diethylene glycol, triethylene glycol, tetraethylene glycol and mixtures thereof and the process is conducted at a temperature of 80° to 300° C.

2. A process according to claim 1, wherein said fluorinating agent is admixed with cesium fluoride.

3. A process according to claim 1, wherein 2.01 to 2.5 equivalents of fluorinating agent based on 3-chloro-2-(chloromethyl)-propene, are employed.

4. A process according to claim 1, wherein 2.03 to 2.2 equivalents of fluorinating agent based on 3-chloro-2-(chloromethyl)-propene, are employed.

5. A process according to claim 1, wherein the process is carried out at a temperature of 110° to 180° C.

6. A process according to claim 1, wherein a reaction mixture is obtained which contains (a) 3-fluoro-2-(fluoromethyl)-propane, (b) 3-fluoro-2-(chloromethyl)-propane and (c) 3-chloro-2-(chloro-methyl)-propane and wherein the reaction mixture is worked up by separating (a), (b) and (c) in the sequence of their boiling points by distillation.

7. A process according to claim 6, wherein the 3-fluoro-2-(fluoro-methyl)-propane thus obtained is purified by further distillation.

* * * * *